(12) United States Patent
Singh et al.

(10) Patent No.: US 10,934,269 B2
(45) Date of Patent: *Mar. 2, 2021

(54) PROCESS FOR PREPARATION OF APALUTAMIDE

(71) Applicant: CADILA HEALTHCARE LIMITED, Gujarat (IN)

(72) Inventors: Kumar Kamlesh Singh, Gujarat (IN); Nikhil Amar Singh, Gujarat (IN); Ganpatdan Shimbhu Charan, Gujarat (IN); Nimeshkumar Mukeshkumar Shah, Gujarat (IN)

(73) Assignee: CADILA HEALTHCARE LIMITED, Gujarat (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/585,007

(22) Filed: Sep. 27, 2019

(65) Prior Publication Data

US 2020/0024250 A1 Jan. 23, 2020

Related U.S. Application Data

(63) Continuation-in-part of application No. 16/366,283, filed on Mar. 27, 2019, now Pat. No. 10,807,965.

(30) Foreign Application Priority Data

Mar. 28, 2018 (IN) .............................. 201821011729
Jan. 4, 2019 (IN) .............................. 201921000421

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
CPC .......................... C07D 401/04; A61K 31/4439
USPC ......... 546/15, 273.1; 514/278, 338; 560/123
See application file for complete search history.

(56) References Cited

U.S. PATENT DOCUMENTS

| 2011/0003839 A1* | 1/2011 | Jung et al. | ......... | A61K 31/4439 514/278 |
| 2018/0201601 A1* | 7/2018 | Chen et al. | .......... | C07D 401/04 546/15 |

* cited by examiner

*Primary Examiner* — Charanjit Aulakh
(74) *Attorney, Agent, or Firm* — Ladas & Parry LLP

(57) ABSTRACT

The present invention relates to a process for the preparation of apalutamide. In particular, the present invention relates to a process for the preparation of apalutamide and its intermediates. The present invention also relates to pharmaceutical compositions comprising apalutamide.

10 Claims, 5 Drawing Sheets

PROCESS FOR PREPARATION OF APALUTAMIDE

CROSS REFERENCE APPLICATION

Figure 1:
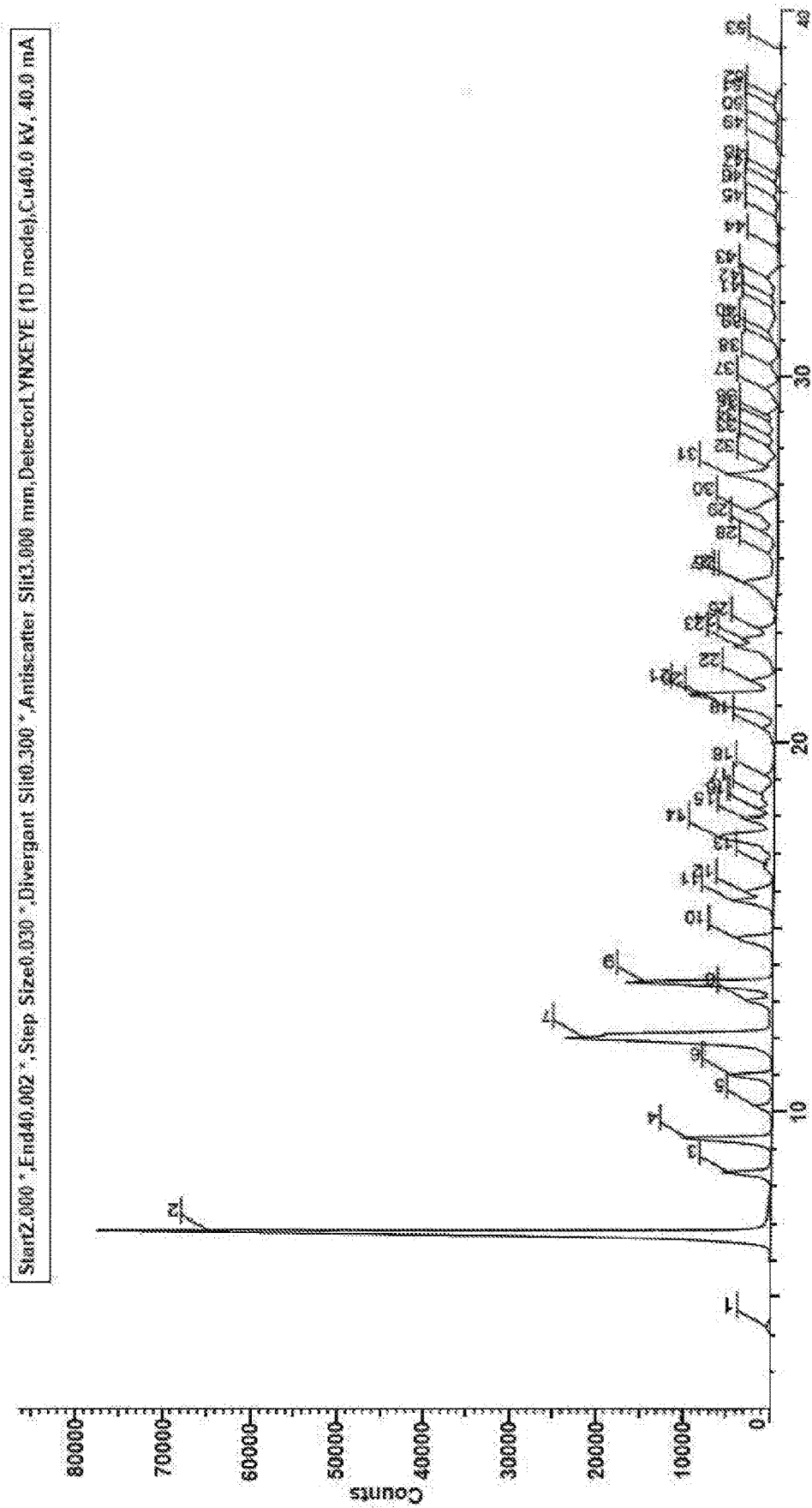

This application is a continuation-in-part of U.S. Ser. No. 16/366,283 filed Mar. 27, 2019, which claims the benefit of Indian Applications Nos.: 201821011729 filed Mar. 28, 2018 and 201921000421 filed Jan. 4, 2019, the content of which are incorporated herein by reference.

FIELD OF THE INVENTION

The present invention relates to a process for the preparation of apalutamide. In particular, the present invention relates to a process for the preparation of apalutamide and its intermediates. The present invention also relates to pharmaceutical composition comprising apalutamide.

BACKGROUND OF THE INVENTION

The following discussion of the prior art is intended to present the invention in an appropriate technical context and allow its significance to be properly appreciated. Unless clearly indicated to the contrary, however, a reference to any prior art in this specification should be construed as an admission that such art is widely known or forms part of common general knowledge in the field.

Apalutamide is an androgen receptor inhibitor, indicated for the treatment of non-metastatic castration-resistant prostate cancer, represented as Formula (I).

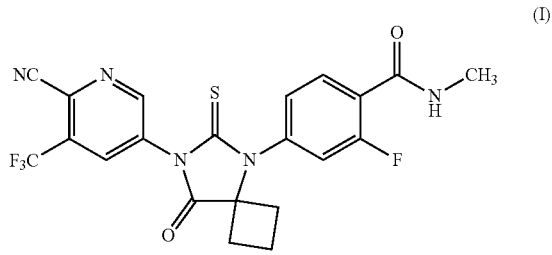 [SMILES: CNC(=O)c1ccc(N2C(=S)N(c3cnc(C#N)c(C(F)(F)F)c3)C(=O)C23CCC3)cc1F]

(I)

U.S. Pat. No. 8,445,507 B2 (the U.S. '507 patent) discloses hydantoin compounds and methods for synthesizing them and using them for preventing or treating a hyperproliferative disorder, such as hormone sensitive prostate cancer or hormone refractory prostate cancer. The U.S. '507 B2 discloses a process for the preparation of apalutamide as depicted in Scheme-1.

Scheme-1

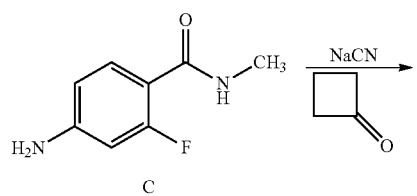

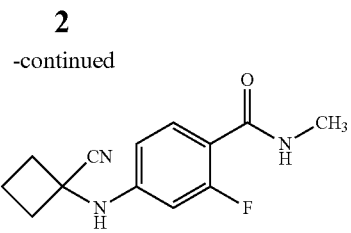

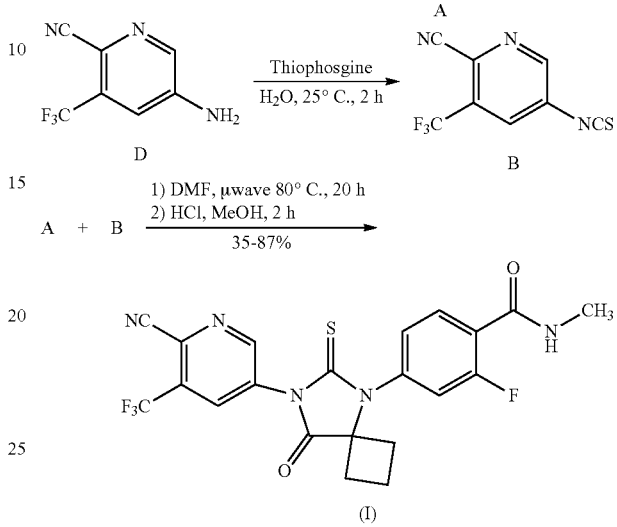

The prior art U.S. '507 B2, discloses the coupling of compound A and compound B with the application of microwave in a polar solvent and with heating to a temperature of about 80° C.

U.S. P.G-Pub. No. 2018/0201601 A1 (the U.S. '601 A1) discloses a process for the preparation of Apalutamide by following reaction scheme:

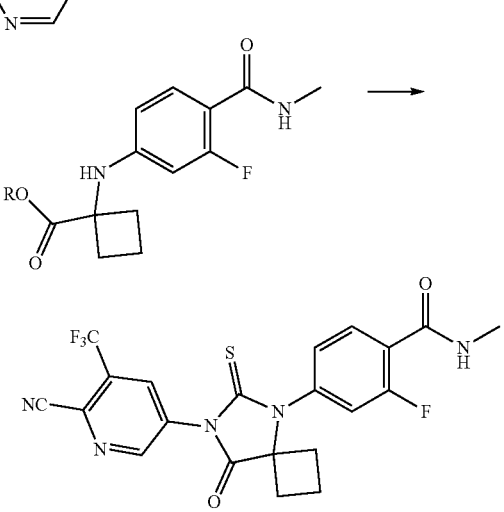

wherein R is $C_1$-$C_6$ alkyl.

There is still a need to provide an alternative process for the preparation of apalutamide.

SUMMARY OF THE INVENTION

In one general aspect, there is provided a process for the preparation of apalutamide of Formula (I), (I)

the process comprising:
reacting compound of Formula (II') or salts thereof, (II')

wherein R is hydrogen or $C_1$-$C_5$ alkyl,
with compound of Formula (III), (III)

optionally in the presence of an alcohol or a phenol or mixture thereof to obtain apalutamide.

In another general aspect, there is provided a process for the preparation of compound Formula (II') or salts thereof, (II')

the process comprising:
reacting compound of Formula (IV) with compound of Formula (V); and (IV) + (V) →1a wherein,
$R_1$ and $R_2$ are either halogen or amine and interchangeable, with the proviso that both $R_1$ and $R_2$ are not same, wherein halogen is F, Cl, Br or I;
R is hydrogen or $C_1$-$C_5$ alkyl;
optionally, converting the compound of Formula (II') to salts thereof.

In another general aspect, there is provided compound of Formula (II'), or salts thereof, (II')

wherein R is hydrogen or $C_1$-$C_5$ alkyl.

In another general aspect, there is provided salts of compound of Formula (II') and its use for the preparation of apalutamide.

In another general aspect, there is provided a process for the preparation of salts of compound of Formula (II') and its use for the preparation of apalutamide. The process comprising reacting compound of Formula (II') with a base in a suitable solvent to obtain salt of compound Formula (II').

In another general aspect, there is provided a process for isolation of compound of Formula (III) in solid form and its use for the preparation of apalutamide.

In another general aspect, there is provided a substantially pure apalutamide.

In another general aspect, there is provided an apalutamide of Formula (I) substantially free from diketo-impurity-A.

In another general aspect, there is provided an apalutamide of Formula (I) substantially free from desflouro-impurity-B.

In another general aspect, there is provided an apalutamide of Formula (I) substantially free from one or more of impurities when measured by area percentage of HPLC.

In another general aspect, there is provided a pharmaceutical composition comprising substantially pure apalutamide together with one or more of pharmaceutically acceptable carriers, excipients, and diluents.

In another general aspect, there is provided a pharmaceutical composition comprising apalutamide substantially free from one or more of impurities together with one or more of pharmaceutically acceptable carriers, excipients, and diluents.

DETAILED DESCRIPTION OF THE DRAWINGS

FIG. 1: XRD of triethylamine salt of compound of Formula (II)

Figure 2:
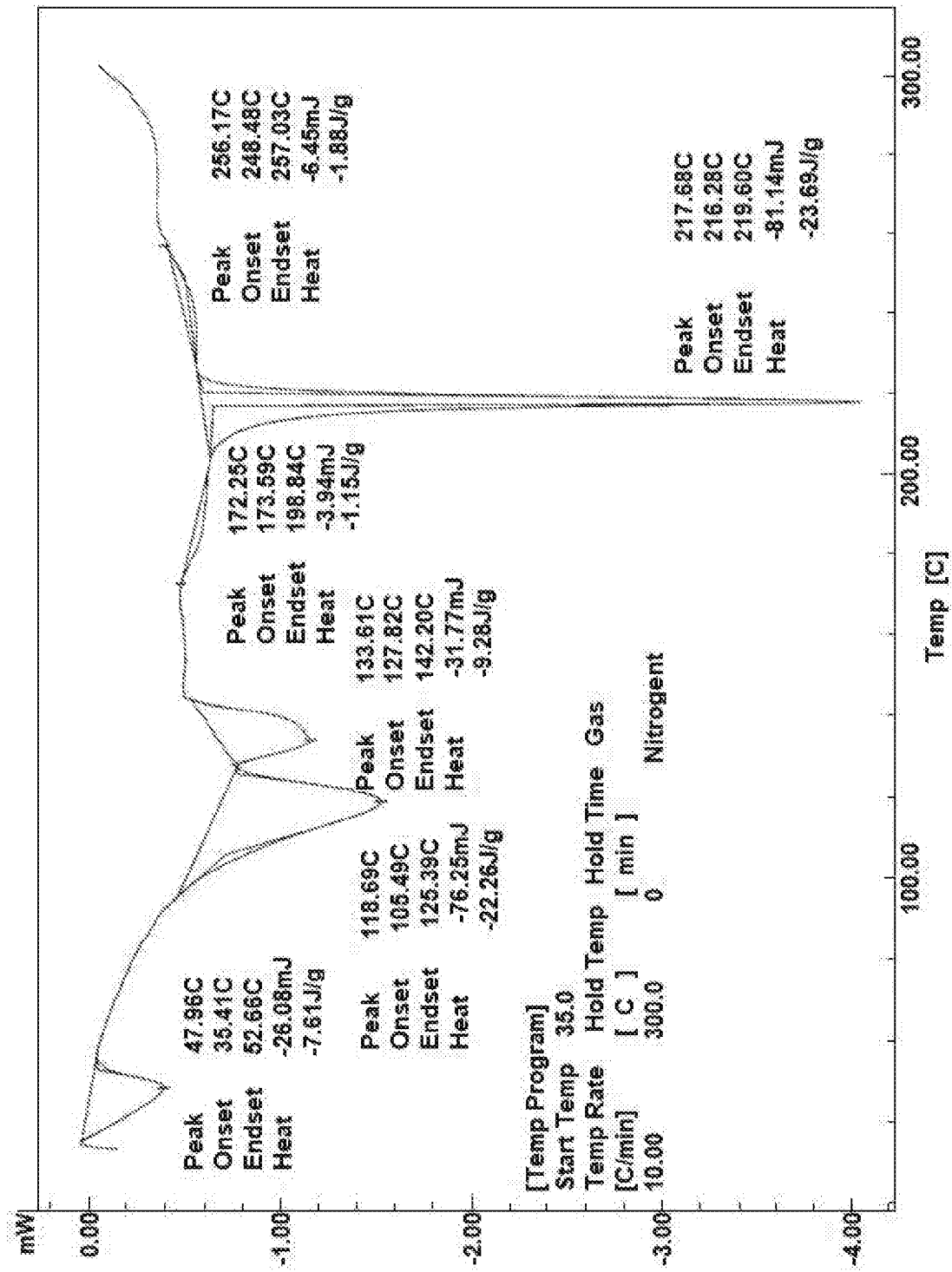

FIG. 2: DSC thermogram of triethylamine salt compound of Formula (II)

Figure 3:
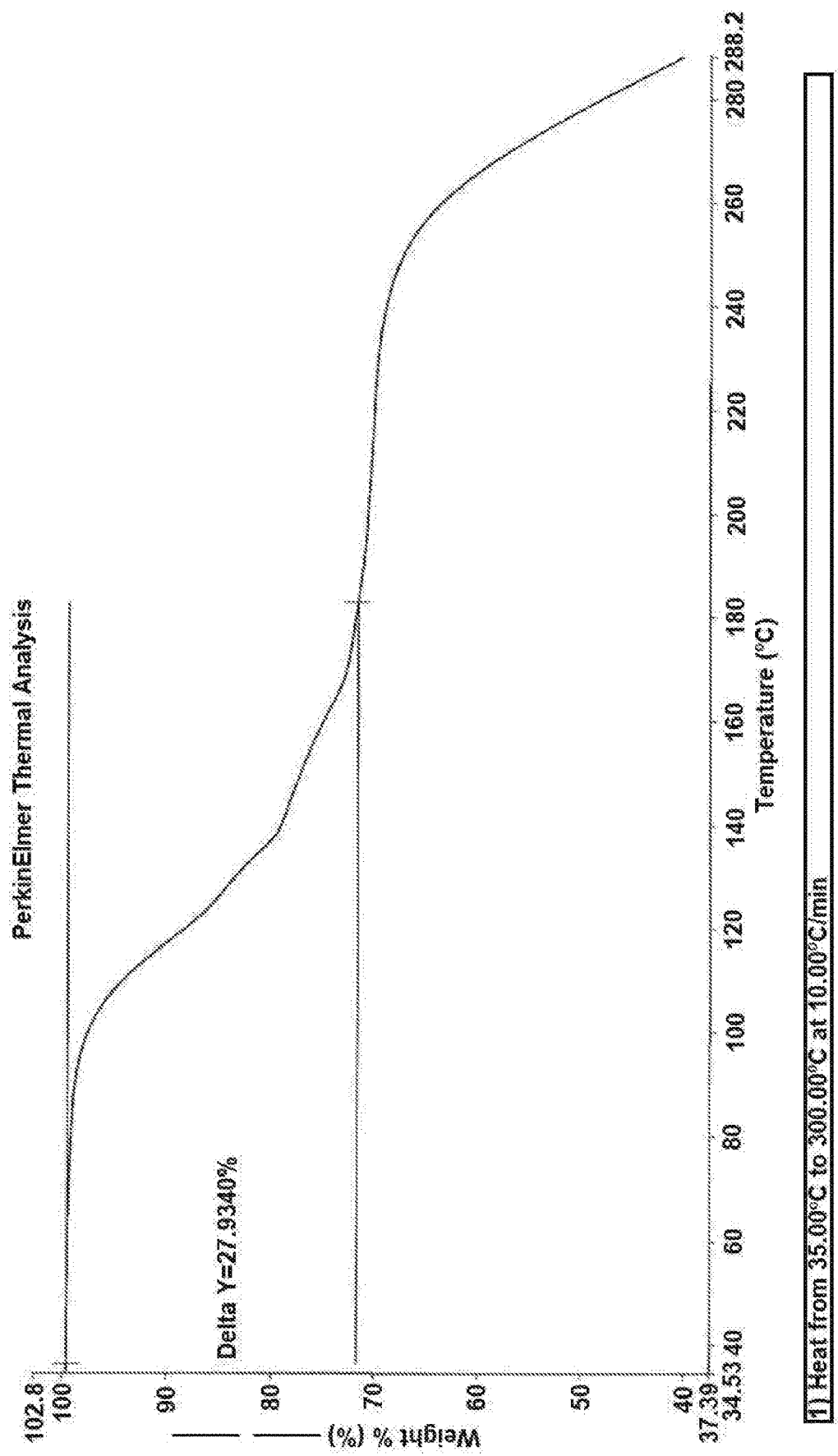

FIG. 3: TGA of triethylamine salt compound of Formula (II)

Figure 4:
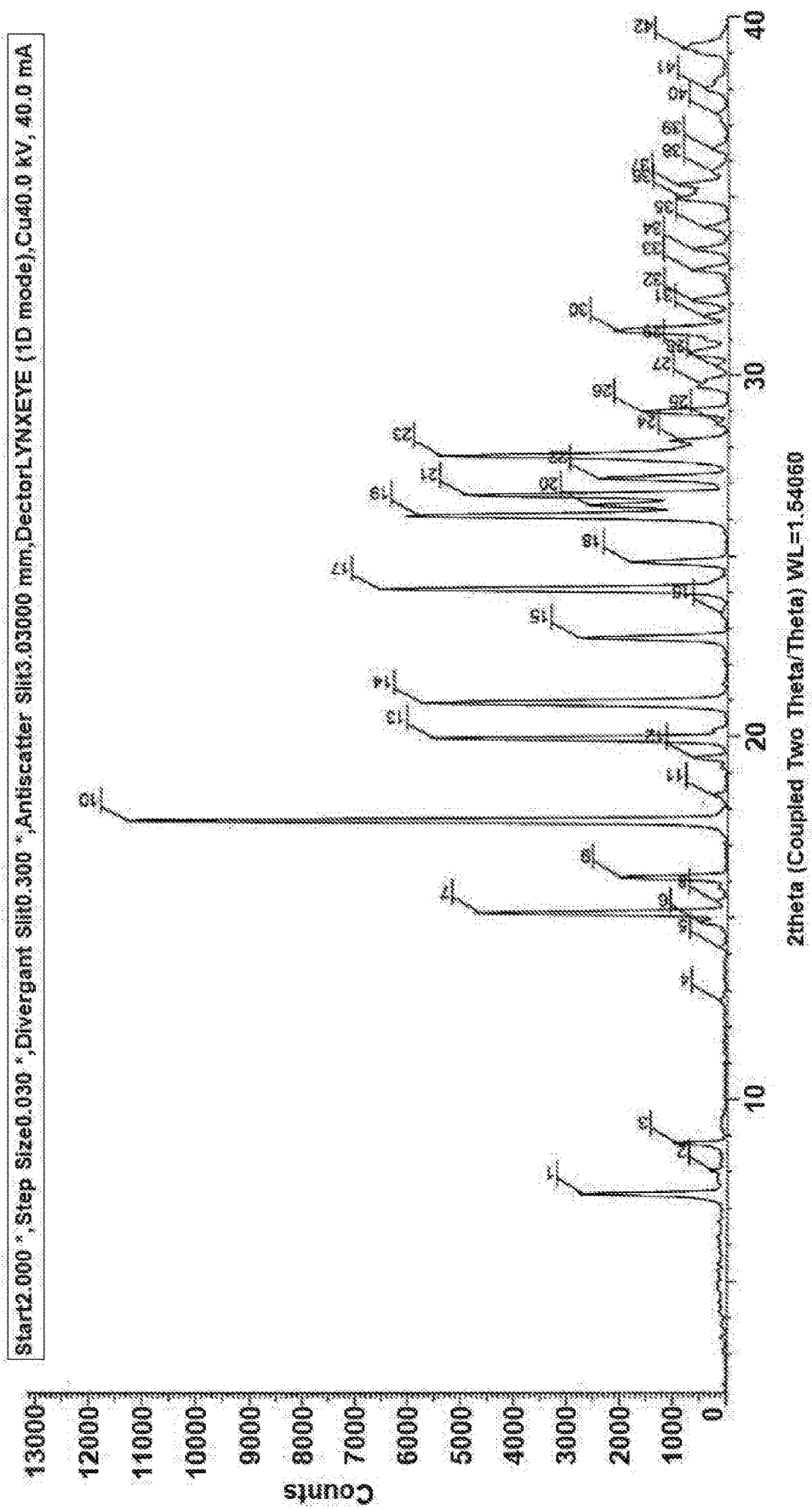

FIG. 4: XRD of compound of Formula (III)

Figure 5:
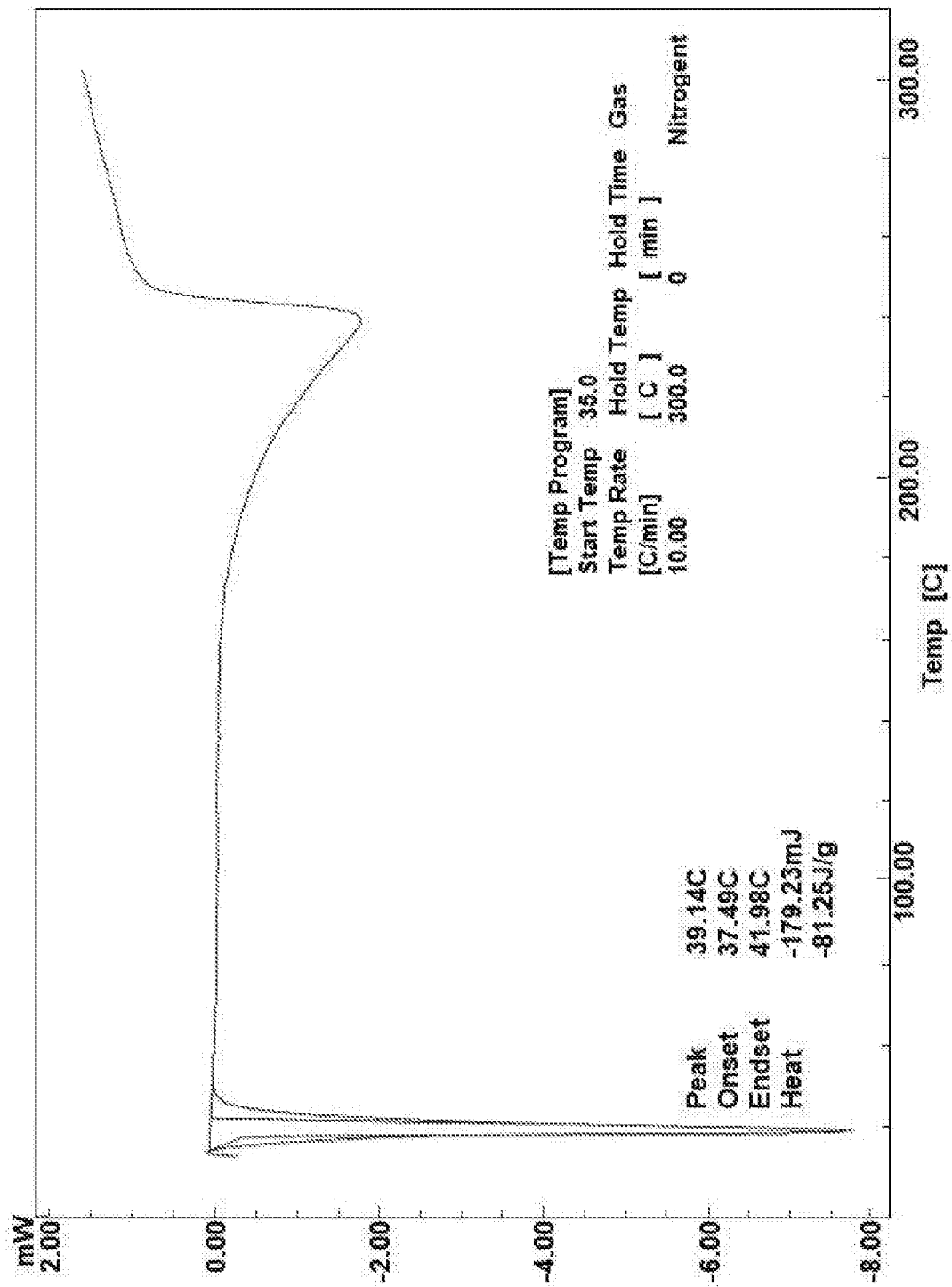

FIG. 5: DSC thermogram of compound of Formula (III)

DETAILED DESCRIPTION OF THE INVENTION

All ranges recited herein include the endpoints, including those that recite a range "between" two values. Terms such as "about", "generally", and "substantially," are to be construed as modifying a term or value such that it is not an absolute. This includes, at very least, the degree of expected experimental error, technique error and instrument error for a given technique used to measure value.

The terms such as "treating", "reacting", and "condensing" have meanings as widely used by general prior art in the field of invention and can be easily understood by those skilled in the art.

The product(s) obtained may further be dried additionally to achieve the desired level of moisture and/or residual solvents. The product(s) obtained may further be converted to any other physical forms thereof which include but not specifically limited to polymorph(s), salt(s), solvate(s), hydrate(s), co-crystal(s) or solid dispersion(s); and crystalline or amorphous forms thereof.

In general, the term "substantially free" means apalutamide having purity of about 98% or more having each one or more of impurities less than 0.15% or less by area percentage of HPLC. In particular, the apalutamide prepared the present invention is having purity of about 98% or more, 99% or more, 99.5% or more, 99.8% or more, 99.9% or more and having diketo impurity-A of about 0.15% or less, 0.10% or less, 0.05% or less or not in detectable amount, when measured by area percentage of HPLC.

The term "substantially pure" herein means apalutamide having a purity of at least about 98% by area percentage of HPLC. In particular, apalutamide having a purity of at least about 99%, more particularly, a purity of at least about 99.5%, further more particularly, a purity of at least about 99.8%, most particularly, a purity of at least about 99.9% by area percentage of HPLC.

As used herein, the term "solution" or "reaction mixture" does not limit to a clear solution only and includes any hazy or opaque mass obtained.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The terms used throughout the description is defined herein below.

"TEA" refers to triethylamine.
"TBA" refers to ten-butyl amine.
"DIPA" refers to diisopropyl amine.
"DIPEA" refers to diisopropyl ethylamine.
"DBU" refers to 1,8-diazabicyclo[5.4.0]undec-7-ene.
"DABCO" refers to 1,4-diazabicyclo[2.2.2]octane.
"DBN" refers to 1,5-Diazabicyclo[4.3.0]non-5-ene "HPLC" refers to high performance liquid chromatography.

In one general aspect, there is provided a process for the preparation of apalutamide of Formula (I),

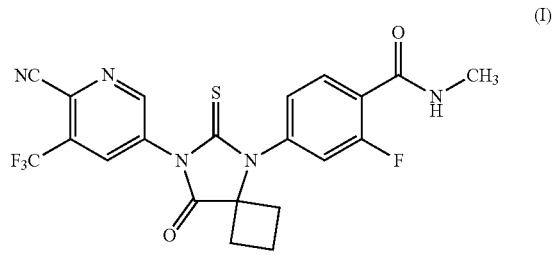 [SMILES: CNC(=O)c1ccc(N2C(=S)N(c3cnc(C#N)c(C(F)(F)F)c3)C(=O)C23CCC3)cc1F]

the process comprising:
reacting compound of Formula (II') or salts thereof,

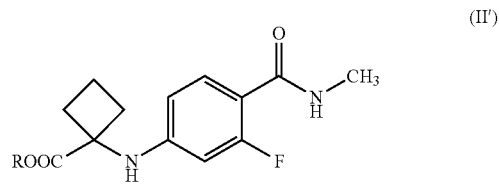

wherein R is hydrogen or $C_1$-$C_5$ alkyl,
with compound of Formula (III),

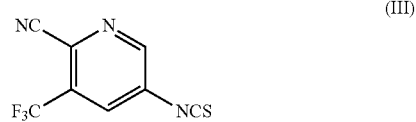

optionally in the presence of an alcohol or a phenol or mixture thereof to obtain apalutamide.

In another general aspect, there is provided a process for the preparation of compound
Formula (II') or salts thereof,

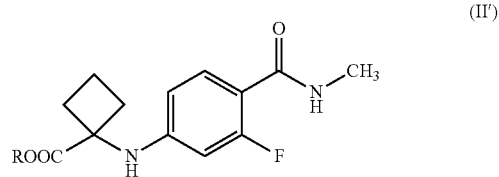

the process comprising:
reacting compound of Formula (IV) with compound of Formula (V); and

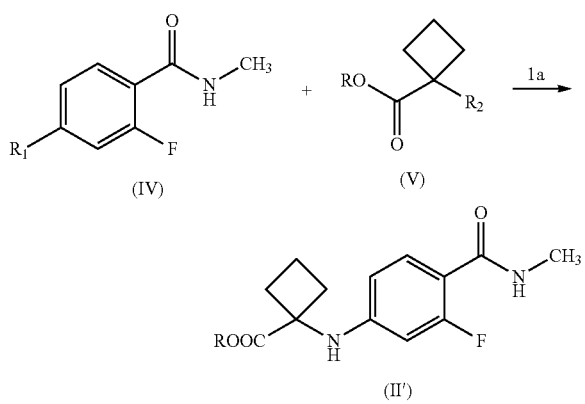

wherein,

R$_1$ and R$_2$ are either halogen or amine and interchangeable, with the proviso that both R$_1$ and R$_2$ are not same, wherein halogen is F, Cl, Br or I;

R is hydrogen or C$_1$-C$_5$ alkyl;

optionally, converting the compound of Formula (II') to salts thereof.

In another general aspect, there is provided a process for the preparation of apalutamide of Formula (I),

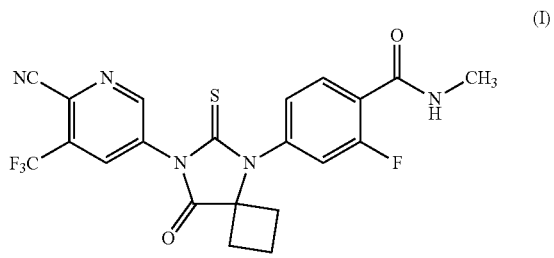 [SMILES: CNC(=O)c1ccc(N2C(=S)N(c3cnc(C#N)c(C(F)(F)F)c3)C(=O)C23CCC3)cc1F]

the process comprising:
reacting triethylamonium salt compound of Formula (IIs),

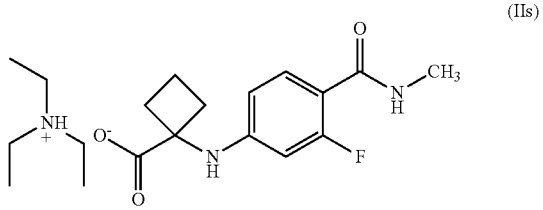

with compound of Formula (III),

optionally in the presence of an alcohol or a phenol or mixture thereof to obtain apalutamide.

In general, the compound of Formula (IV) is reacted with compound of Formula (V) optionally in the presence of a base, in one or more solvents to obtain compound of Formula (II).

The base comprises of inorganic or organic base. The inorganic base comprises one or more of sodium hydroxide, potassium hydroxide, lithium hydroxide; sodium carbonate, potassium carbonate, sodium bicarbonate, potassium bicarbonate; and ammonia or its aqueous solution; or the organic base comprises one or more of TEA, TBA, DIPA, DIPEA, pyridine, piperidine, morpholine, DBU, DABCO and DBN. In particular, TEA may be used.

The solvent comprises one or more of esters selected from ethyl acetate, isopropyl acetate, t-butyl acetate, and isobutyl acetate; hydrocarbons selected from toluene, xylene, ethyl benzene, heptane, hexane, and cyclohexane; chlorinated solvents selected from chloroform, methylene dichloride, ethylene dichloride, chlorobenzene, chloroform, and carbon tetrachloride. In particular, toluene, xylene, methylene dichloride, and ethyl acetate may be used.

In general, the purification of compound (II) may be performed in one or more of solvents. The solvent comprises one or more of ketones selected from acetone, methyl isobutyl ketone, and methyl ethyl ketone; esters selected from ethyl acetate, isopropyl acetate, t-butyl acetate, and isobutyl acetate; chlorinated solvents selected from methylene dichloride, ethylene dichloride, and chlorobenzene; and water. In particular, water, methanol, acetone, ethyl acetate, methylene dichloride may be used. More particularly, water is used.

In general, the compound of Formula (III) can be prepared by reacting 5-amino-3-(trifluoromethyl)picolinonitrile with thiophosgene in the presence of a solvent. The solvent comprises one or more of ketones selected from acetone, methyl isobutyl ketone, and methyl ethyl ketone; esters selected from ethyl acetate, isopropyl acetate, t-butyl acetate, and isobutyl acetate; chlorinated solvents selected from chloroform, methylene dichloride, ethylene dichloride, and chlorobenzene. hi particular, a mixture of methylene dichloride and water may be used.

In general, the salts of compound of Formula (II') may be prepared by reacting compound of Formula (II') with base, optionally in the presence of one or more solvents.

The salts of compound Formula (II') may include salts with inorganic bases such as sodium hydroxide, potassium hydroxide, lithium hydroxide; sodium carbonate, potassium carbonate, sodium bicarbonate and potassium bicarbonate; or the organic base comprising one or more of TEA, TBA, DIPA, DIPEA, pyridine, piperidine, morpholine, DBU, DABCO and DBN; or the inorganic acids such as hydrochloric acid, sulfuric acid, nitric acid, perchloric acid, phosphoric acid; or the organic acids such as acetic acid, oxalic acid, citric acid, formic acid. In particular, TEA may be used.

In general, the apalutamide of Formula (I) may be prepared by reacting the compound of Formula (II') or its salts with the compound of Formula (III), optionally in the presence of a base in one or more solvents.

In general, the base comprises of inorganic or organic base. The inorganic base comprises one or more of sodium hydroxide, potassium hydroxide, lithium hydroxide; sodium carbonate, potassium carbonate, sodium bicarbonate, and potassium bicarbonate; or the organic base comprises one or more of TEA, TBA, DIPA, DIPEA, pyridine, piperidine, morpholine, DBU, DABCO and DBN. In particular, TEA may be used.

In general, the solvent comprises of one or more of esters selected from ethyl acetate, isopropyl acetate, t-butyl acetate, and isobutyl acetate; hydrocarbons selected from toluene, xylene, ethyl benzene, heptane, hexane, and cyclohexane; chlorinated solvents selected from methylene dichloride, ethylene dichloride, chlorobenzene, chloroform, and carbon tetrachloride. In particular, toluene, xylene, methylene dichloride, and ethyl acetate may be used.

The prior art U.S. '507 B2, discloses the coupling of compound A and compound B with application of microwave in a polar solvent and with heating to a temperature of about 80° C. The present invention has advantages over the prior art. The process is simple and doesn't involve use of microwave.

In general, the reaction of compound (II) and compound (III) may be performed at temperature ranging from 25° C. to boiling point of the solvent(s). In particular, the reaction may be performed at 25° C. to 150° C. Alternatively, the reaction may also be performed under cooled conditions having temperature from −25° C. to about 25° C. In particular, from −10° C. to about 10° C.

In general, the present invention provides the preparation of apalutamide wherein the reaction of the compound (II') and the compound (III) is done in presence of an alcohol or phenol. The alcohol or phenol arrest the formation of impurity-A during the reaction and thereby provide apalutamide substantially free from impurity-A.

In general, the alcohol or phenol is selected from 2,2,2-trifluoroethanol, methanol, ethanol, n-propyl alcohol, isopropyl alcohol, cyclohexanol, isobutyl alcohol, tort-amyl alcohol, butanol, pentanol, hexadecanol, ethane-1,2-diol, propane-1,2-diol, phenol, cresol, or mixture thereof. In particular, 2,2,2-trifluoro ethanol may be used.

The compound of Formula (D i.e. apalutamide may be isolated by usual work-up wherein the solvent after completion of the reaction may be removed by filtration or evaporation.

Alternatively, the solvent may be distilled to obtain residue which may be extracted with one or more solvents selected from dimethylformamide, dimethylacetamide, dimethylsulfoxide, N-methyl pyrrolidone, tetrahydrofuran, acetonitrile, ethylacetate, toluene, and xylene. The reaction mixture may be acidified with an acid selected from hydrochloric acid, sulfuric acid, acetic acid, or formic acid, thereby to adjust the acidic pH.

In general, the purification of apalutamide is done in one or more of solvents. The organic solvents comprise one or more of alcohols selected from methanol, ethanol, isopropanol, butanol, t-butanol, and isoamylalcohol; ketones selected from acetone, methyl isobutyl ketone, and methyl ethyl ketone; esters selected from ethyl acetate, isopropyl acetate, t-butyl acetate, and isobutyl acetate; chlorinated solvents selected from methylene dichloride, ethylene dichloride, and chlorobenzene. In particular, methanol, acetone, ethyl acetate, methylene dichloride may be used.

In another general aspect, there is provided a compound of Formula (II'), or salts thereof,

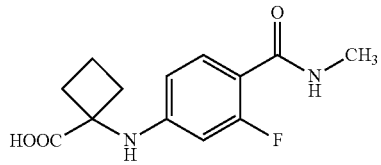 [SMILES: CNC(=O)c1ccc(NC2(C(=O)O)CCC2)cc1F]

(II')

wherein R is hydrogen or $C_1$-$C_5$ alkyl.

In another general aspect, there is provided salts of compound of Formula (II') and its use for the preparation of apalutamide.

In another general aspect, there is provided an isolated compound of Formula (II'), or salts thereof.

In another general aspect, there is provided an isolated compound of Formula (II):

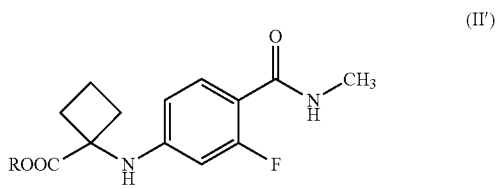

In general, the compound of Formula (II) may be isolated by usual work-up wherein the solvent after completion of the reaction may be removed by filtration or evaporation. Alternatively, the solvent may be distilled to obtain residue which may be extracted with one or more solvents selected from water, dichloromethane, chloroform, dimethylformamide, dimethylacetamide, dimethylsulfoxide, N-methyl pyrrolidone, tetrahydrofuran, acetonitrile, ethylacetate, toluene, and xylene. The reaction mixture may be acidified with an acid selected from hydrochloric acid, sulfuric acid, acetic acid, or formic acid, thereby to adjust the acidic pH.

In another general aspect, there is provided a salt compound of Formula (IIs):

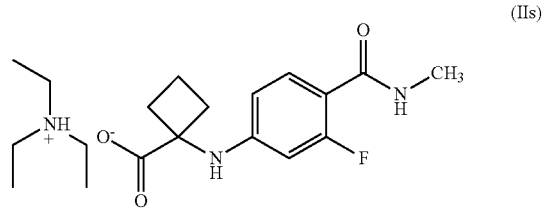

(IIs)

In general, the salt compound of Formula (IIs) of the present invention is crystalline, characterized by x-ray powder diffraction pattern having peaks expressed in terms of 2θ at about 6.7°, 12.0° and 13.5°±0.2. It can be further characterized by peaks expressed in terms of 2θ at about 9.3°, 17.5°, 21.1° and 21.2°±0.2. The XRD, DSC, and TGA of compound of Formula (II) as triethylamine salt is depicted in FIGS. 1, 2 & 3.

In another general aspect, there is provided a process for the preparation of salts of compound of Formula (II') and its use for the preparation of apalutamide. The process comprising reacting compound of Formula (II') with a base in a suitable solvent to obtain salt of compound Formula (II').

The salts of compound Formula (II') may include salts with inorganic bases such as sodium hydroxide, potassium hydroxide, lithium hydroxide; sodium carbonate, potassium carbonate, sodium bicarbonate and potassium bicarbonate; or the organic base comprising one or more of TEA, TBA, DIPA, DIPEA, pyridine, piperidine, morpholine, DBU, DABCO and DBN; or the inorganic acids such as hydrochloric acid, sulfuric acid, nitric acid, perchloric acid, phosphoric acid; or the organic acids such as acetic acid, oxalic acid, citric acid, formic acid. In particular, TEA may be used.

In another general aspect, there is provided a process for isolation of compound of Formula (III) in solid form and its use for the preparation of apalutamide.

In another general aspect, there is provided a process for isolation of compound of Formula (III) in solid form through crystallization.

The solvent used for crystallization may include non-polar solvents such hexane; cyclohexane, heptane; toluene or polar solvents such as acetone, ethanol, diethyl ether, methyl tertiary butyl ether or butanol. The XRD and DSC of compound of Formula (III) is depicted in FIGS. 4 & 5.

In general, the compound of Formula (III) of the present invention is characterized by x-ray powder diffraction pattern having peaks expressed in terms of 2θ at about 15.1°, 17.7°, 19.9° and 20.9°±0.2. It can be further characterized by peaks expressed in terms of 2θ at about 7.3°, 15.1°, 16.1°, 22.8°, 26.1°, 26.7° and 27.1°±0.2.

In general, the compound of Formula (III) of the present invention is characterized by DSC. DSC measures the difference in heat energy uptake between a sample and an appropriate reference with increase in temperature. The DSC thermogram for compound of Formula (III) is shown in FIG. 5 and described in example 8, indicates an endothermic peak at about 39.1° C.

In another general aspect, there is provided a substantially pure apalutamide.

In another general aspect, there is provided a process for the preparation of apalutamide of Formula (I),

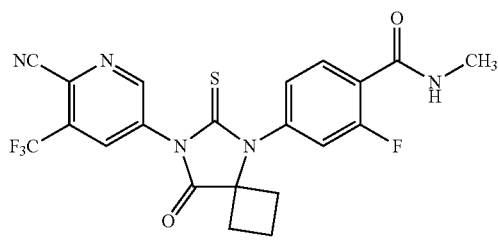

the process comprising:
reacting a compound of Formula (IV) with a compound of Formula (V) to obtain compound of Formula (II');

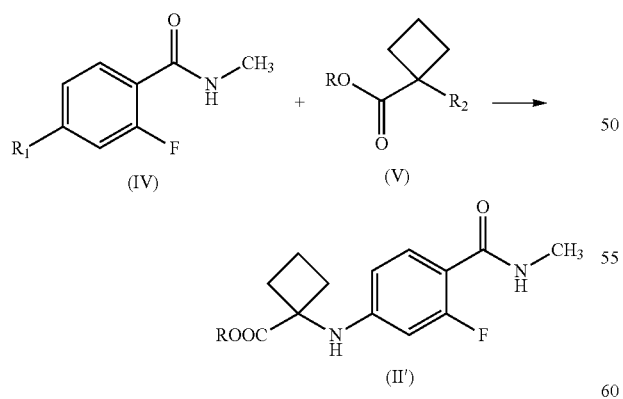

wherein, $R_1$ and $R_2$ are either a leaving group or amine and interchangeable, with a proviso that both $R_1$ and $R_2$ are not same, and wherein the leaving group is F, Cl, Br or I, OTs, OTf, OMs,
optionally, converting the compound of Formula (II') to salts thereof;

reacting 5-amino-3-(tri fluoromethyl)picolinonitrile with thiophosgene to obtain compound of Formula (III); and

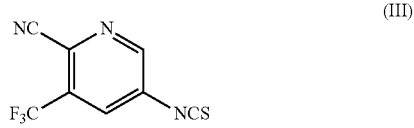

reacting the compound of Formula (III) in-situ with the compound of Formula (II') or salts thereof in the presence of an alcohol or phenol to obtain apalutamide of Formula (I).

In general, the compound of Formula (II') or salts thereof is the compound of Formula (IIs),

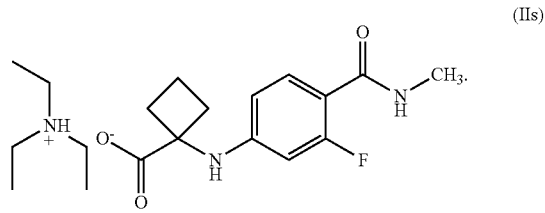

In general, the compound of Formula (III) is not isolated and reacted in-situ with compound of Formula (II') or salts thereof in the presence of alcohol or phenol selected from 2,2,2-trifluoroethanol methanol, ethanol, n-propyl alcohol, isopropyl alcohol, cyclohexanol, isobutyl alcohol, tert-amyl alcohol, butanol, pentanol, hexadecanol, ethane-1,2-diol, propane-1,2-diol, phenol, cresol, or mixture thereof.

In general, the impurities of apalutamide may be one or more of impurity-A or impurity-B represented by structural formula as herein below:

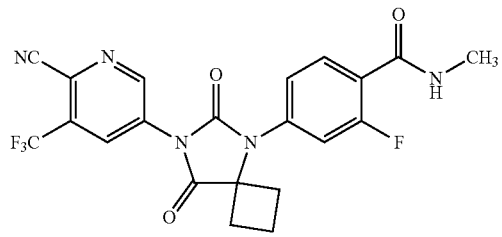

(Diketo-Impurity-A)

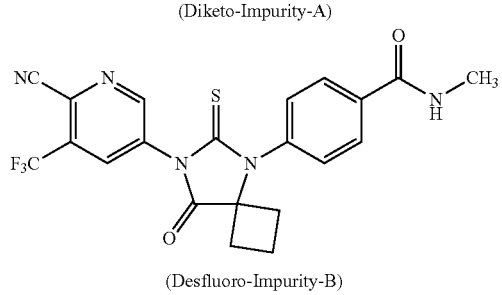

(Desfluoro-Impurity-B)

In another general aspect, there is provided an apalutamide of Formula (I) substantially free from diketo-impurity-A.

In another general aspect, there is provided an apalutamide of Formula (I) substantially free from desflouro-impurity-B.

In general, the starting compound (II), wherein R is hydrogen, is the potential source for the formation of desflouro-impurity-B. Preparation of salt of compound of Formula (II) provides compound of Formula (II) in its salt form substantially free from impurities. The presence of higher amount of desfluoro analoque of the compound (II) results in higher content of impurity-B, when measured by area percentage of HPLC.

The use of starting material compound (H) containing desfluoro analogue of about 0.15% or less, results in apalutamide containing desfluoro-impurity-B of about 0.15% or less by area percentage of HPLC.

In general, the starting material compound (II) or its salt containing desfluoro analogue of about 0.15% or less, in particular, containing 0.10% or less, more particular, containing 0.05% or less, most particularly containing not in detectable amount may be used to obtain apalutamide substantially free from desfluoro-impurity-B.

In another general aspect, there is provided an apalutamide of Formula (I) substantially free from one or more of impurities when measured by area percentage of HPLC.

In another general aspect, there is provided a pharmaceutical composition comprising substantially pure apalutamide together with one or more of pharmaceutically acceptable carriers, excipients, and diluents.

In another general aspect, there is provided a pharmaceutical composition comprising apalutamide substantially free from one or more of impurities together with one or more of pharmaceutically acceptable carriers, excipients, and diluents.

The present invention is further illustrated by the following example which is provided merely to be exemplary of the invention and do not limit the scope of the invention.

EXAMPLES

Example-1: Preparation of 1-((3-fluoro-4-(methylcarbamoyl)phenyl)amino)-cyclobutane-1-carboxylic Acid In a 500 mL four necked round bottomed flask equipped with nitrogen atmosphere facility, mechanical stirrer, thermometer and an addition funnel, (20 g) 4-amino-2-fluoro-N-methylbenzamide, (25.6 g) 1-bromocyclobutane-1-carboxylic acid and 200 mL chloroform were added at room temperature. (40 mL) triethylamine was added and the reaction mixture was stirred for 15 hours at 60-65° C. After the completion of the reaction, the reaction mixture was cooled to 25-35° C. and 20 mL water followed by addition of 20 mL hydrochloric acid and stirred for 2 hours, filtered, washed with 25 mL water and dried to obtain 20.1 g titled compound with 98.85% purity by HPLC.

Example-2: Preparation of 1-((3-fluoro-4-(methylcarbamoyl)phenyl)amino)-cyclobutane-1-carboxylic Acid In a 500 mL four necked round bottomed flask equipped with nitrogen atmosphere facility, mechanical stirrer, thermometer and an addition funnel, (10 g) 4-amino-2-fluoro-N-methylbenzamide, (12.8 g) -bromocyclobutane-1-carboxylic acid and 100 mL chloroform were added at room temperature. (15 g) triethylamine was added and the reaction mixture was stirred for 15 hours at 60-65° C. After the completion of the reaction, the reaction mixture was cooled to 25-35° C. and 10 mL hydrochloric acid was added and stirred for 2 hours, filtered, washed with 25 mL water and dried to obtain 10.2 g titled compound with 97.99% purity by HPLC.

Example-3: Preparation of 1-((3-fluoro-4-(methylcarbamoyflphenyDamino)-cyclobutane-1-carboxylic Acid In a 500 mL four necked round bottomed flask equipped with nitrogen atmosphere facility, mechanical stirrer, thermometer and an addition funnel, (10 g) 4-amino-2-fluoro-N-methylbenzamide, (16 g) 1-bromocyclobutane-1-carboxylic acid and 100 mL dichloromethane were added at room temperature. (25 mL) triethylamine was added and the reaction mixture was stirred for 15 hours at 20-30° C. After the completion of the reaction, the reaction mixture was concentrated completely U/V at 40° C. 100 mL water was added and stirred for 1 hour. 7.5 mL hydrochloric acid was added and stirred for 30 min. The reaction mixture was cooled to 0-5° C. and stirred for 1 hour, filtered, washed with 25 mL water and dried to obtain 15 g titled compound with 94.05% purity by HPLC.

Example-4: Purification of 1-((3-fluoro-4-(methylcarbamoyl)phenyl)amino)-cyclobutane-1-carboxylic Acid In a 500 mL four necked round bottomed flask equipped with nitrogen atmosphere facility, mechanical stirrer, thermometer and an addition funnel, (15 g) title compound of example-1 and 120 mL acetone were heated to 55 to 60° C. for 1 hour. The reaction mixture was cooled to 0 to 5° C. and the product thus obtained was filtered and dried under vacuum at 50° C. to obtain 12.1 g titled compound with 99.50% purity by HPLC.

Example-5: Preparation of 1-((3-fluoro-4-(methylcarbamoyl)phenyl)amino)-cyclobutane-1-carboxylate Triethylammonium In a 500 mL four necked round bottomed flask equipped with nitrogen atmosphere facility, mechanical stirrer, thermometer and an addition funnel, (18 g) 1-((3-fluoro-4-(methylcarbamoyl)phenyl)amino)cyclobutane-1-carboxylic acid, 270 mL ethyl acetate and 18 mL triethylamine were added at room temperature. The reaction mixture was stirred for 2 hours at 25 to 35° C., filtered, washed with 36 mL ethyl acetate and dried to obtain 23.93 g titled compound with 99.81% purity by HPLC.

Example-6: Preparation of 1-((3-fluoro-4-(methylcarbamoyl)phenyl)amino)-cyclobutane-1-carboxylate Triethylammonium In a 500 mL four necked round bottomed flask equipped with nitrogen atmosphere facility, mechanical stirrer, thermometer and an addition funnel, (10 g) 1-((3-fluoro-4-(methylcarbamoyl)phenyl)amino)cyclobutane-1-carboxylic acid, 100 mL ethyl acetate and 10 mL triethylamine were added at room temperature. The reaction mixture was stirred for 2 hours at 25 to 35° C., filtered, washed with 25 mL ethyl acetate and dried to obtain 16 g titled compound with 99.7% purity by HPLC.

Example-7: Preparation of 1-((3-fluoro-4-(methylcarbamoyl)phenyl)amino)-cyclobutane-1-carboxylate Potassium In a 500 mL four necked round bottomed flask equipped with nitrogen atmosphere facility, mechanical stirrer, thermometer and an addition funnel, (10 g) 1-((3-fluoro-4-(methylcarbamoyl)phenyl)amino)cyclobutane-1-carboxylic acid, 100 mL ethyl acetate and 5 g of potassium hydroxide dissolved in 10 mL water were added at room temperature. The reaction mixture was stirred for 2 hours at 25 to 35° C., filtered, washed with 25 mL ethyl acetate and dried to obtain 16 g titled compound with 99.7% purity by HPLC.

Example-8: Preparation of 5-isothiocyanato-3-(trifluoromethyl)picolinonitrile

In a 500 mL four necked round bottomed flask equipped with nitrogen atmosphere facility, mechanical stirrer, thermometer and an addition funnel, (20 g) 5-amino-3-(trifluoromethyl)picolinonitrile, 200 mL water and 100 mL dichloromethane were added at 20-30° C. The reaction mixture was stirred for 15 min and 20 mL thiophosgene was added. The reaction mixture was stirred for 4 hours. After completion of the reaction, the layers were separated. Organic layer washed with 100 mL 8% sodium bicarbonate solution and the organic layer was concentrated completely U/V at 40° C. 140 mL n-hexane was added to the concentrated reaction mass and cooled 0 to 5° C. The compound was filtered, washed with hexane and dried to obtain as solid 20 g titled compound with 96.52% purity by HPLC.

Example-9: Preparation of 5-isothiocyanato-3-(trifluoromethyl)picolinonitrile

In a 500 mL four necked round bottomed flask equipped with nitrogen atmosphere facility, mechanical stirrer, thermometer and an addition funnel, (15 g) 5-amino-3-(trifluoromethyl)picolinonitrile, 150 mL water and 75 mL dichloromethane were added at 20-30° C. The reaction mixture was stirred for 15 min and 9 mL thiophosgene was added. The reaction mixture was stirred for 4 hours. After completion of the reaction, the layers were separated and the organic layer was concentrated completely U/V at 40° C. 105 mL hexane was added to the concentrated reaction mass and cooled 0 to 5° C. The compound was filtered, washed with hexane and dried to obtain 19.85 g titled compound.

Example-10: Preparation of Apalutamide

In a 1000 mL four necked round bottomed flask equipped with nitrogen atmosphere facility, mechanical stirrer, thermometer, condenser and an addition funnel (16 g) 5-isothiocyanato-3-(trifluoromethyl)picolinonitrile and 200 mL chloroform were added. (10 g) phenol was added into the reaction mixture. The reaction mixture was stirred for 15 min. The reaction mixture was heated to 60 to 65° C. A solution of (20 g) 1-((3-fluoro-4-(methylcarbamoyl)phenyl)amino)cyclobutane-1-carboxylate triethylammonium in 200 mL chloroform was added slowly at 60 to 65° C. The reaction mixture was refluxed for 3 hours. After the completion of the reaction, the reaction mixture was washed by 100 mL water and concentrated the organic layer completely at 50° C. U/V. 180 mL methanol followed by 60 mL water were added to the concentred reaction mass and stirred for 3 hours at 25-35° C. The compound was filtered, washed with 20 mL of methanol and 20 mL water mixture and dried to obtain 17 g of Apalutamide with 98.81% purity by HPLC.

Example-11: Purification of Apalutamide

In a 500 mL four necked round bottomed flask equipped with nitrogen atmosphere facility, mechanical stirrer, thermometer and an addition funnel (15 g) Apalutamide and (105 mL) methanol were added at 20-30° C. The reaction mixture was heated to reflux to obtain clear solution. The reaction mixture was cooled to 0 to 5° C. and stirred for 1 hour. The Apalutamide was filtered, washed with 30 mL methanol and dried to obtain 11.2 g Apalutamide with 99.82% purity having 0.01% of diketo impurity and 0.03% of single maximum unknown impurity by HPLC.

Example-12: Preparation of Apalutamide

In a 50 mL four necked round bottomed flask equipped with nitrogen atmosphere facility, mechanical stirrer, thermometer and an addition funnel (1 g) 1-((3-fluoro-4-(methylcarbamoyl)phenyl)amino)cyclobutane-1-carboxylate triethylammonium and 10 mL chloroform were added. (1 g) phenol was added in to the reaction mixture. The reaction mixture was stirred for 15 min. The reaction mixture was heated to reflux. A solution of (1 g) 5-isothiocyanato-3-(trifluoromethyl)5 picolinonitrile in 10 mL chloroform was added slowly. The reaction mixture was refluxed for 6 hours. After the completion of the reaction, the reaction mixture was concentrated completely at 50° C. U/V. 20 mL isopropyl alcohol was added to the concentred reaction mass and stirred for 3 hours at 20-30° C. The compound was filtered, washed with 2 mL of isopropyl alcohol and dried to obtain 1 g of Apalutamide with 99.18% purity by HPLC having diketo impurity-A <0.15.

Example-13: Preparation of Apalutamide

In a 50 mL four necked round bottomed flask equipped with nitrogen atmosphere facility, mechanical stirrer, thermometer and an addition funnel (1 g) 1-((3-fluoro-4-(methylcarbamoyl)phenyl)amino)cyclobutane-1-carboxylate triethylammonium and 10 mL chloroform were added. The reaction mixture was heated to reflux. A solution of (1 g) 5-isothiocyanato-3-(trifluoromethyl)picolinonitrile in 10 mL chloroform was added slowly. The reaction mixture was refluxed for 6 hours. After the completion of the reaction, the reaction mixture was concentrated completely at 50° C. U/V. 20 mL isopropyl alcohol was added to the concentred reaction mass and stirred for 3 hours at 20-30° C. The compound was filtered, washed with 2 mL of isopropyl alcohol and dried to obtain 0.9 g of Apalutamide with 98.5% purity and having 0.5% of diketo impurity-A by HPLC.

Example-14: Preparation of Apalutamide in Absence of Phenol

In a 500 mL four necked round bottomed flask equipped with nitrogen atmosphere facility, mechanical stirrer, thermometer and an addition funnel (14 g) 5-isothiocyanato-3-(trifluoromethyl)picolinonitrile and 150 mL chloroform were added. The reaction mixture was stirred for 15 min and 5 mL triethylamine was added at 20-30° C. The reaction mixture was heated to reflux for 15 min. (10 g) 1-((3-fluoro-4-(methylcarbamoyl)phenyl)amino)cyclobutane-1-carboxylic acid was added. The reaction mixture was refluxed for 6 hours. After the completion of the reaction, the reaction mixture was concentrated completely at 50° C. U/V. 20 mL isopropyl alcohol was added to the concentered reaction mass and stirred for 60 min at 20-30° C. The compound was filtered, washed with 2 mL of isopropyl alcohol and dried to obtain 13.7 g of apalutamide with 98.68% purity by HPLC.

Example-15: Preparation of Apalutamide in Presence of Phenol

In a 500 mL four necked round bottomed flask equipped with nitrogen atmosphere facility, mechanical stirrer, thermometer and an addition funnel (14 g) 5-isothiocyanato-3-(trifluoromethyl)picolinonitrile and 150 mL chloroform were added. (10 g) phenol was added into the reaction mixture. The reaction mixture was stirred for 15 min and 5 mL triethylamine was added at 20-30° C. The reaction mixture was heated to reflux for 15 min. (10 g) 1-((3-fluoro-4-(methylcarbamoyl)-phenyl)amino)cyclobutane-1-carboxylic acid was added. The reaction mixture was refluxed for 6 hours. After the completion of the reaction, the reaction mixture was concentrated completely at 50° C. U/V. 20 mL isopropyl alcohol was added to the concentered reaction mass and stirred for 60 min at 20-30° C. The compound was filtered, washed with 2 mL of isopropyl alcohol and dried to obtain 14.6 g of apalutamide with 99.82% purity having diketo impurity-A <0.1% by HPLC.

Example-16: Purification of Apalutamide

In a 500 mL four necked round bottomed flask equipped with nitrogen atmosphere facility, mechanical stirrer, thermometer and an addition funnel (12 g) apalutamide and (180 mL) isopropyl alcohol were added at 20-30° C. The reaction mixture was heated to reflux to obtain clear solution. (240 mg) activated Norit-A carbon. The reaction mixture was stirred for 15 to 30 min at 70-75° C. The reaction mixture was cooled to 20-30° C. and stirred for 1 hour. The apalutamide was filtered, washed with 2 mL isopropyl alcohol and dried to obtain 10.45 g apalutamide with 99.85% purity by HPLC.

Example 17: Preparation of Apalutamide in Presence of 2,2,2-trifluoroethanol In a 500 mL four necked round bottomed flask equipped with nitrogen atmosphere facility, mechanical stirrer, thermometer and an addition funnel 5-isothiocyanato-3-(trifluoromethyl)picolinonitrile (4 g) and 50 mL chloroform were added. (0.68 g) 2,2,2-trifluoroethanol was added in to the reaction mixture. The reaction mixture was heated to reflux and the solution of 1-((3-fluoro-4-(methylcarbamoyl)phenyl)-amino)cyclobutane-1-carboxylate triethylammonium (5 g) in chloroform (50 mL) was added in reaction mixture. The reaction mixture was refluxed for 2 hours. After the completion of the reaction, the reaction mixture was filtered, washed filtrate with water (25 mL) and concentrated organic layer at 50° C. U/V. 45 mL methanol and 5 mL water was added to the concentered reaction mass and stirred for 60 min at 0-5° C. The compound was filtered, washed with 10 mL water and dried to obtain 3.9 g of Apalutamide with 99.55% purity by HPLC and diketo impurity 0.14% by HPLC.

Example 18: Preparation of 5-isothiocyanato-3-(trifluoromethyl)-picolinonitrile In a 1 L four necked round bottomed flask equipped with nitrogen atmosphere facility, mechanical stirrer, thermometer and an addition funnel, 5-amino-3-(trifluoromethyl) picolinonitrile (40 g), 400 mL water and 200 mL dichloromethane were added at 25-35° C. The reaction mixture was stirred for 15 min and 24.6 mL thiophosgene was added. The reaction mixture was stirred for 4 hours at 35-40° C. After completion of the reaction, the layers were separated and the organic layer was concentrated completely U/V at 40° C. to obtain titled compound as syrup and forwarded to next step without isolation.

Example 19: Preparation of Apalutamide

In a 500 mL four necked round bottomed flask equipped with nitrogen atmosphere facility, mechanical stirrer, thermometer and an addition funnel 5-isothiocyanato-3-(trifluoromethyl)picolinonitrile (obtained in example-18) and 500 mL chloroform were added. (6.8 g) 2,2,2-trifluoroethanol was added into the reaction mixture. The reaction mixture was heated to reflux and (50 g) solution of 1-((3-fluoro-4-(methylcarbamoyl)phenyl)amino)cyclobutane-1-carboxylate triethylammonium in chloroform (500 ml) was added in reaction mixture. The reaction mixture was refluxed for 2 hours. After the completion of the reaction, the reaction mixture was filtered, washed the filtrate with water (250 ml) and concentrated organic layer at 50° C. U/V. 450 mL methanol and 50 ml water was added to the concentered reaction mass and stirred for 60 min at 0-5° C. The compound was filtered, washed with 150 mL mixture of aqueous methanol and dried to obtain 38.7 g of Apalutamide with 99.67% purity by HPLC and diketo impurity 0.05% by HPLC.

While the present invention has been described in terms of its specific embodiments, certain modification and equivalents will be apparent to those skilled in art and the intended to be included within the scope of the invention.

We claim:

1. A process for the preparation of apalutamide of Formula (I),

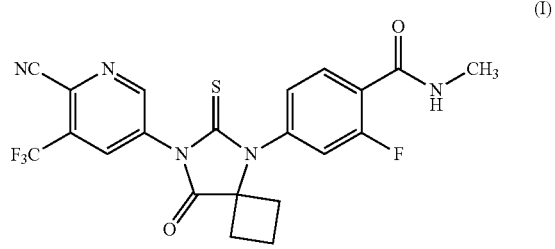 [SMILES: CNC(=O)c1ccc(N2C(=S)N(c3cnc(C#N)c(C(F)(F)F)c3)C(=O)C23CCC3)cc1F]

the process comprising:
reacting a compound of Formula (II'), or salts thereof,

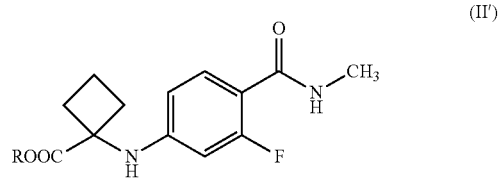

wherein R is hydrogen or $C_1$-$C_5$ alkyl,
with a compound of Formula (III),

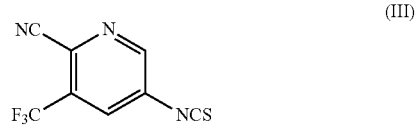

in the presence of an alcohol or phenol to obtain the apalutamide of Formula (I).

2. The process according to claim 1, wherein the alcohol or phenol is 2,2,2-trifluoro ethanol methanol, ethanol, n-propyl alcohol, isopropyl alcohol, cyclohexanol, isobutyl alcohol, tert-amyl alcohol, butanol, pentanol, hexadecanol, ethane-1,2-diol, propane-1,2-diol, phenol, cresol, or mixture thereof.

3. The process according to claim 1, wherein the compound of Formula (II') is prepared by a process comprising reacting a compound of Formula (IV) with a compound of Formula (V);

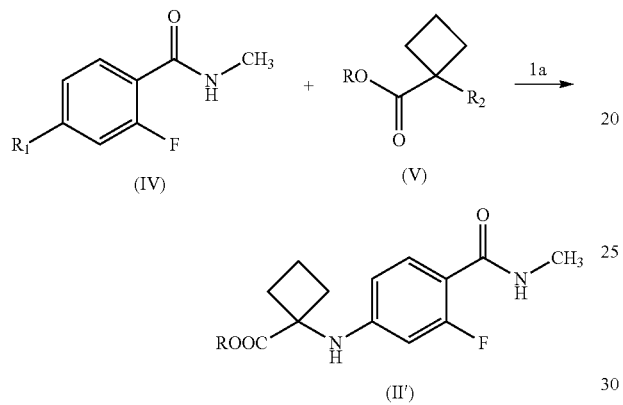

wherein, $R_1$ and $R_2$ are either a leaving group or amine and interchangeable, with a proviso that both $R_1$ and $R_2$ are not same, and wherein the leaving group is F, Cl, Br, I, OTs, OTf, or OMs and R is hydrogen or $C_1$-$C_5$ alkyl optionally, converting the compound of Formula (II') to salts thereof.

4. The process according to claim 1, wherein the compound of Formula (II') is compound of Formula (Hs),

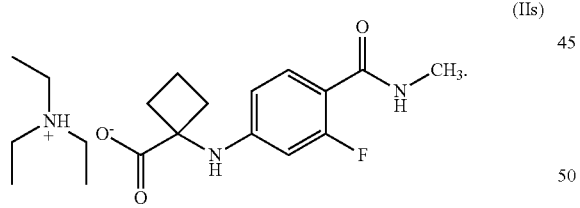

5. A process for the preparation of apalutamide, the process comprising reacting a compound of Formula (Hs),

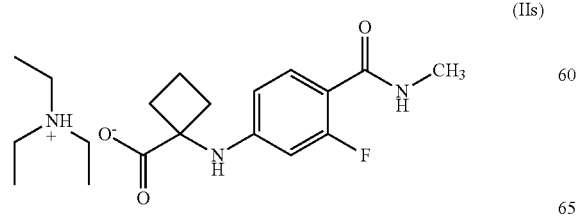

with a compound of Formula (III),

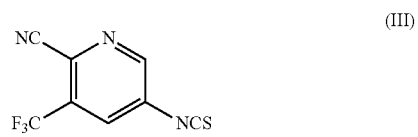

in the presence of alcohol or phenol or mixture thereof to obtain apalutamide of Formula (I).

6. The process according to claim 5, wherein the alcohol or phenol is 2,2,2-trifluoro ethanol methanol, ethanol, n-propyl alcohol, isopropyl alcohol, cyclohexanol, isobutyl alcohol, tert-amyl alcohol, butanol, pentanol, hexadecanol, ethane-1,2-diol, propane-1,2-diol, phenol, cresol, or mixture thereof.

7. The process according to claim 1, wherein the process comprising:

reacting a compound of Formula (IV) with a compound of Formula (V) to obtain a compound of Formula (II');

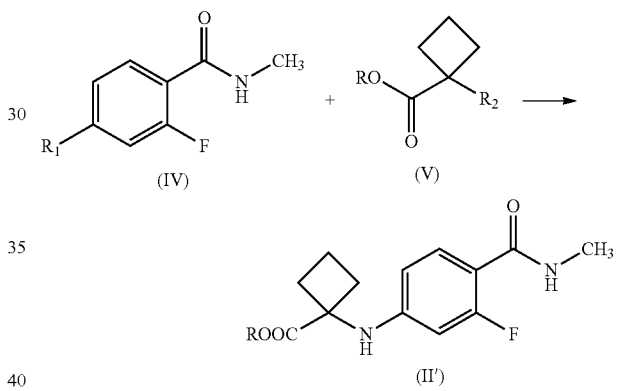

wherein, $R_1$ and $R_2$ are either a leaving group or amine and interchangeable, with a proviso that both $R_1$ and $R_2$ are not same, and wherein the leaving group is F, Cl, Br, I, OTs, OTf, or OMs and R is hydrogen or $C_1$-$C_5$ alkyl;

optionally, converting the compound of Formula (II') to salts thereof;

reacting 5-amino-3-(trifluoromethyl)picolinonitrile with thiophosgene to obtain compound of Formula (III); and

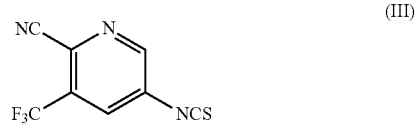

reacting the compound of Formula (III) in-situ with the compound of Formula (II') or salts thereof in the presence of an alcohol or phenol to obtain apalutamide of Formula (I).

8. The process as claimed in claim 7, wherein the compound of Formula (II') or salts thereof is the compound of Formula (Hs),

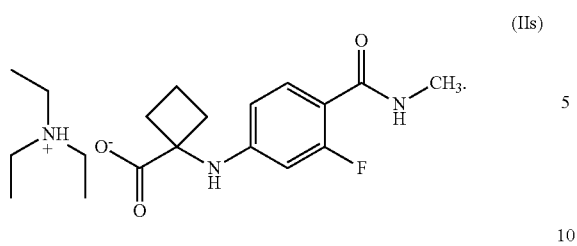

(IIs)

9. The process as claimed in claim 7, wherein the compound of Formula (III) is not isolated and reacted in-situ with compound of Formula (II') or salts thereof.

10. The process as claimed in claim 7, wherein the alcohol or phenol is selected from 2,2,2-trifluoroethanol methanol, ethanol, n-propyl alcohol, isopropyl alcohol, cyclohexanol, isobutyl alcohol, tert-amyl alcohol, butanol, pentanol, hexadecanol, ethane-1,2-diol, propane-1,2-diol, phenol, cresol, or mixture thereof.

* * * * *